(12) United States Patent
Shmukler et al.

(10) Patent No.: US 11,413,135 B2
(45) Date of Patent: Aug. 16, 2022

(54) INTRAOCULAR LENS SYSTEM

(71) Applicant: EYEMED TECHNOLOGIES LTD, Rishon Le'Zion (IL)

(72) Inventors: Vadim Shmukler, Rishon Le'Zion (IL); Nir Israeli, Kiryat Ono (IL)

(73) Assignee: EYEMED TECHNOLOGIES LTD, Kiryat Ono (IL)

( * ) Notice: Subject to any disclaimer, the term of this patent is extended or adjusted under 35 U.S.C. 154(b) by 31 days.

(21) Appl. No.: 16/620,018

(22) PCT Filed: Jun. 13, 2018

(86) PCT No.: PCT/IL2018/050650
§ 371 (c)(1),
(2) Date: Dec. 6, 2019

(87) PCT Pub. No.: WO2018/229766
PCT Pub. Date: Dec. 20, 2018

(65) Prior Publication Data
US 2020/0197157 A1    Jun. 25, 2020

Related U.S. Application Data

(60) Provisional application No. 62/518,796, filed on Jun. 13, 2017.

(51) Int. Cl.
*A61F 2/16* (2006.01)

(52) U.S. Cl.
CPC .............. *A61F 2/16* (2013.01); *A61F 2/1629* (2013.01); *A61F 2/1632* (2013.01);
(Continued)

(58) Field of Classification Search
None
See application file for complete search history.

(56) References Cited

U.S. PATENT DOCUMENTS

| 4,575,373 A | 3/1986 | Johnson |
| 4,816,031 A | 3/1989 | Pfoff |

(Continued)

FOREIGN PATENT DOCUMENTS

| CN | 1925813 A | 3/2007 |
| CN | 102215781 A | 10/2011 |

(Continued)

OTHER PUBLICATIONS

International Search Report for PCT/IL2018/050650, dated Sep. 17, 2018.

(Continued)

*Primary Examiner* — Leslie Lopez
(74) *Attorney, Agent, or Firm* — ISUS Intellectual Property PLLC; Anthony Jason Mirabito

(57) ABSTRACT

Lens support structure for supporting an intraocular lens (IOL) is provided, the lens support structure being configured and operable to be securely implanted in a lens capsule of a human eye and hold the IOL in one of a plurality of positions, the support structure comprising a repositioning assembly configured and operable to be activated remotely by a remote energy source and controllably displace the IOL in at least one of directions along and around an optical axis of the IOL, thereby enabling moving the IOL between the plurality of positions. Lens control system is also provided, the control system comprising the lens support structure and a source energy for activating parts thereof. Intraocular lens system is also provided, the system comprising the lens support structure and a lens integrated therein.

16 Claims, 15 Drawing Sheets

(52) U.S. Cl.
CPC ........... *A61F 2002/1689* (2013.01); *A61F 2210/0014* (2013.01); *A61F 2250/0001* (2013.01); *A61F 2250/0004* (2013.01); *A61F 2250/006* (2013.01)

(56) References Cited

U.S. PATENT DOCUMENTS

| | | | |
|---|---|---|---|
| 4,932,966 | A | 6/1990 | Christie et al. |
| 5,108,429 | A | 4/1992 | Wiley |
| 5,203,788 | A | 4/1993 | Wiley |
| 5,443,506 | A | 8/1995 | Garabet |
| 5,728,155 | A * | 3/1998 | Anello .......... A61F 2/1613 623/6.47 |
| 6,884,261 | B2 | 4/2005 | Zadno-azizi et al. |
| 7,122,053 | B2 | 10/2006 | Esch |
| 8,425,599 | B2 | 4/2013 | Shadduck |
| 2008/0046076 | A1 | 2/2008 | Rombach |
| 2011/0112636 | A1 | 5/2011 | Joshua |
| 2012/0323320 | A1 | 12/2012 | Nikolaevich et al. |
| 2014/0200666 | A1 | 7/2014 | Phillips |
| 2015/0272727 | A1 * | 10/2015 | Humayun .......... A61F 2/1635 623/6.39 |
| 2016/0015511 | A1 | 1/2016 | Auld et al. |
| 2016/0235587 | A1 | 8/2016 | Kahook et al. |
| 2016/0278631 | A1 | 9/2016 | Vogler et al. |

FOREIGN PATENT DOCUMENTS

| | | |
|---|---|---|
| CN | 102724933 A | 10/2012 |
| CN | 105792728 A | 7/2016 |
| EP | 2887907 | 7/2019 |
| WO | WO-2016160456 A1 * | 10/2016 .......... A61F 2/1694 |

OTHER PUBLICATIONS

Examination Report—corresponding Indian application 201927053999, dated Mar. 9, 2022, 5 pages.

* cited by examiner

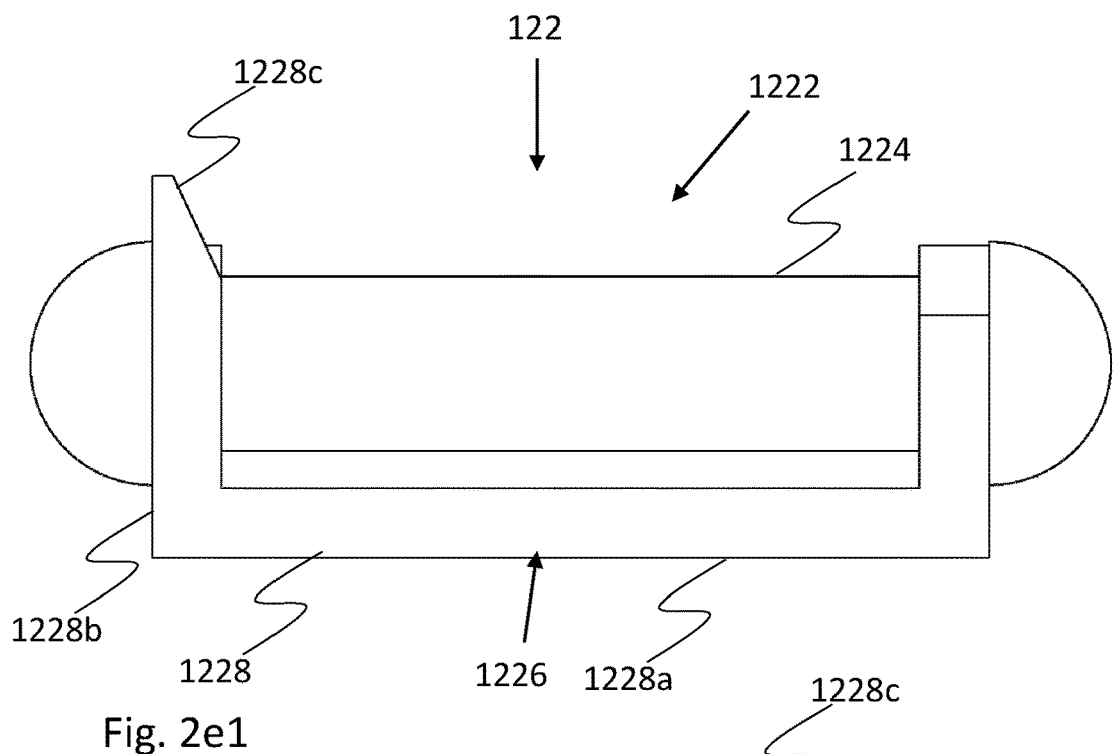
Fig. 2e1
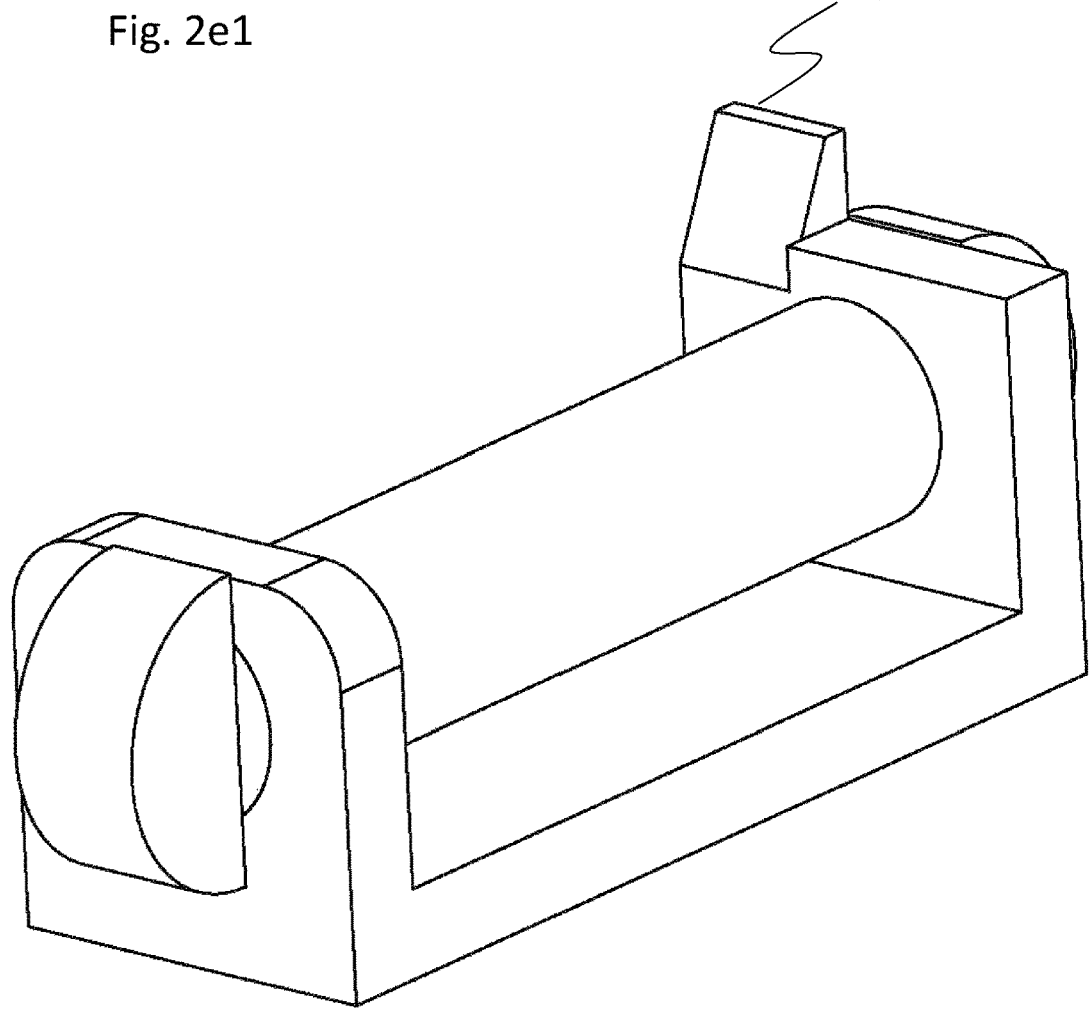
Fig. 2e2

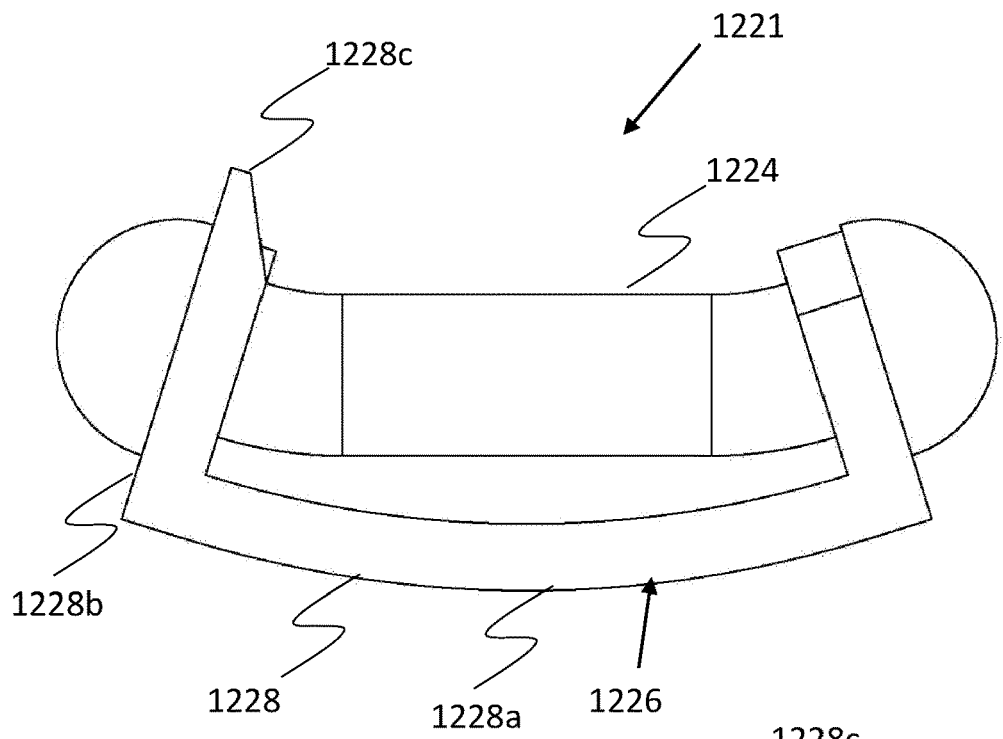
Fig. 2f1
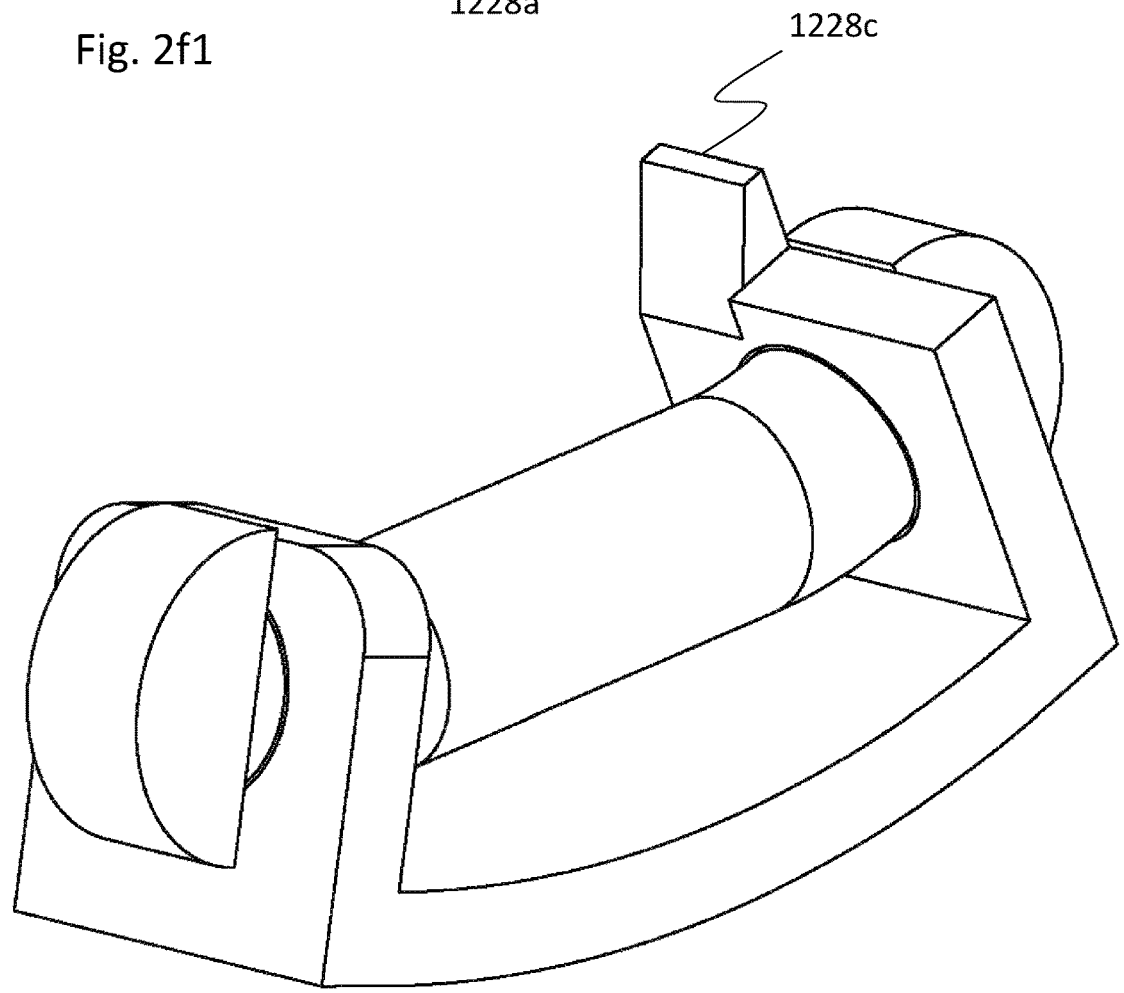
Fig. 2f2

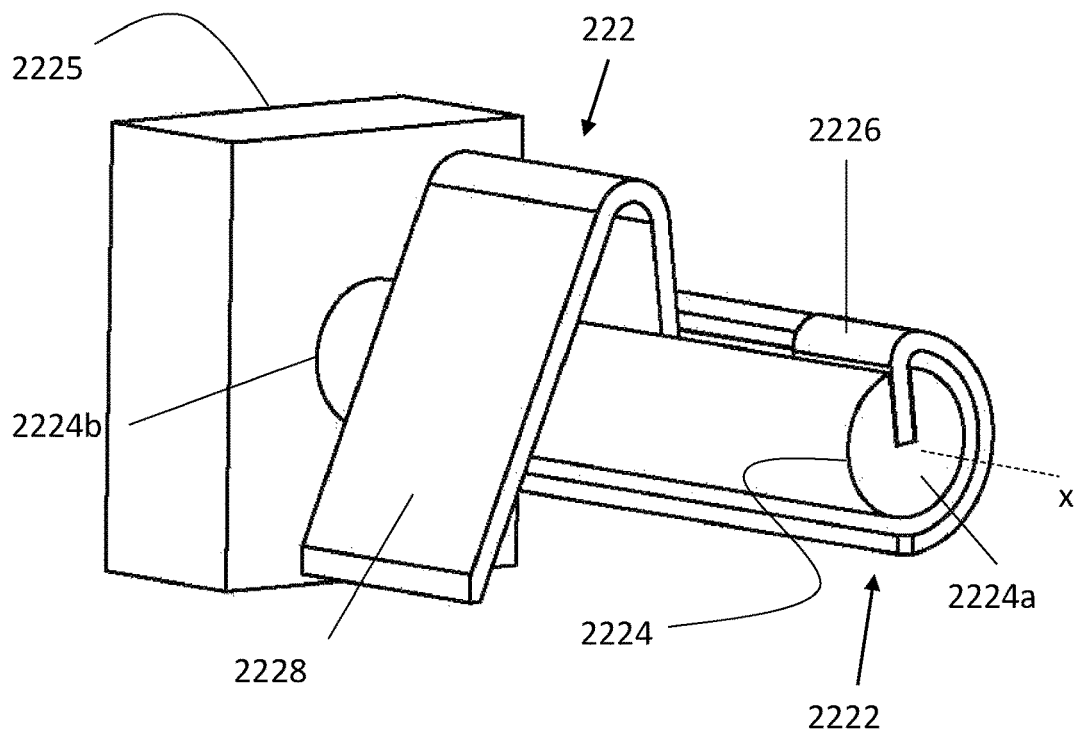
Fig. 3c1
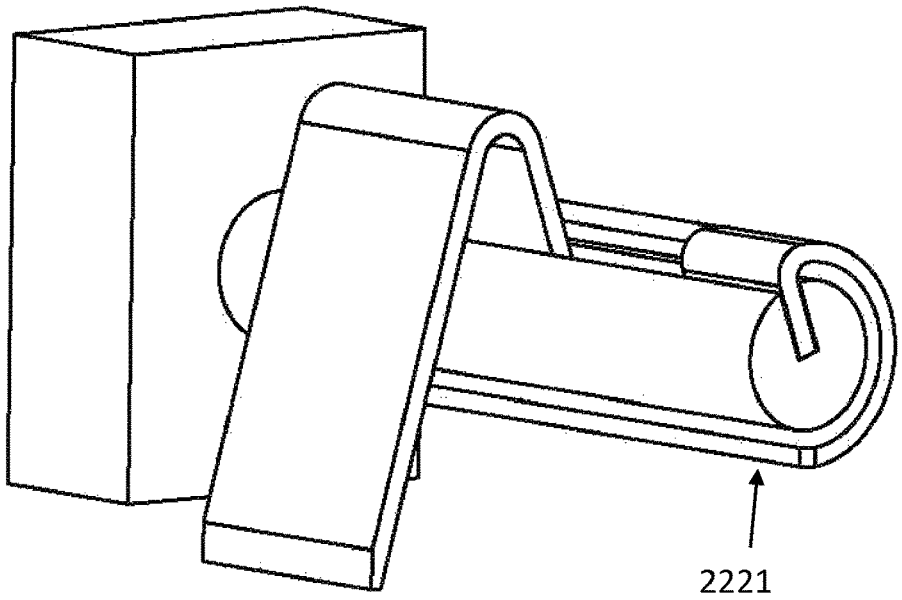
Fig. 3c2

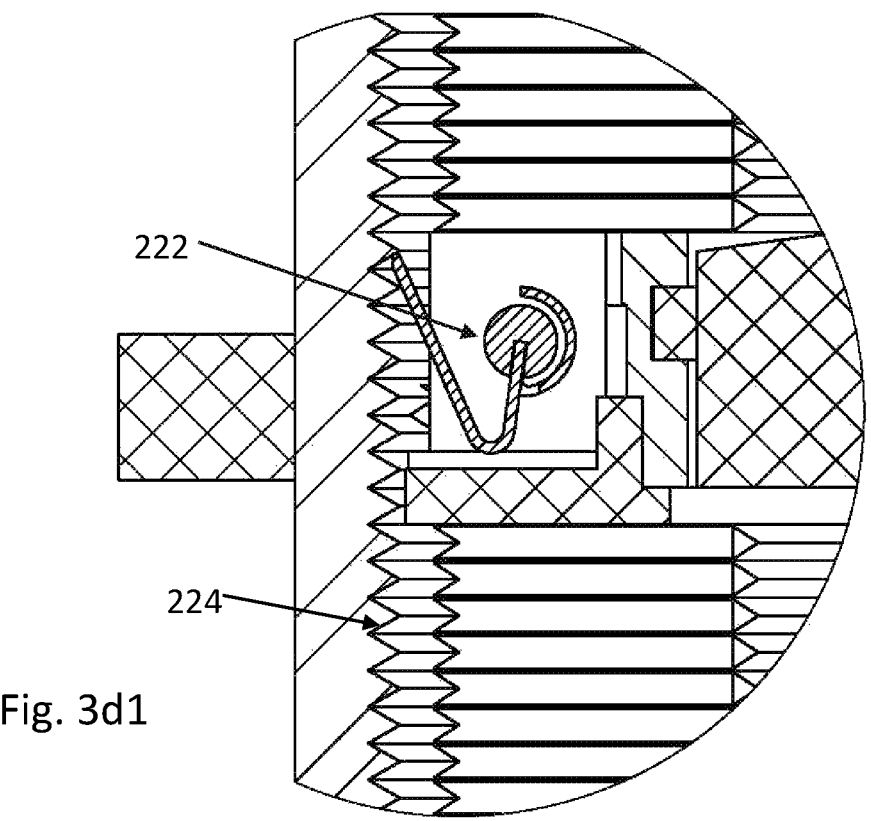
Fig. 3d1
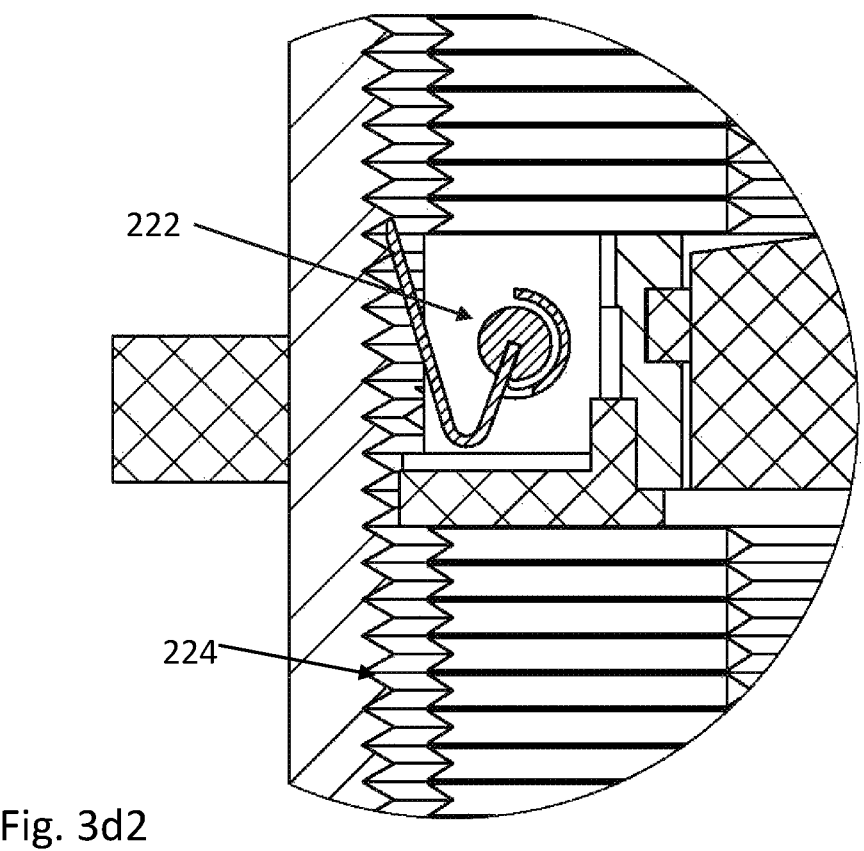
Fig. 3d2

INTRAOCULAR LENS SYSTEM

TECHNOLOGICAL FIELD

The present invention is in the field of medical devices, and relates specifically to intraocular lens devices and systems.

BACKGROUND

Cataracts are the most prevalent ocular disease worldwide, being the cause of half of blindness and third of visual impairment in the world. Annually, 25 million patients require cataract surgery worldwide. When the disability from cataracts affects or alters individual's activities of daily living, a surgical procedure that includes lens removal and intraocular lens (TOL) implantation is the preferred method of treating the functional limitations. In USA, more than 3 million cataract surgical procedures are performed annually, making it the most common surgery for Americans over the age of 65. About 97 percent of cataract surgery patients receive intraocular lens implants.

A cataract is an opacity of a patient's eye lens, whether it is a localized opacity or a diffusive general loss of transparency. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have a fairly good distance vision. However, it is often difficult to predict the exact characteristics of the lens necessary to correct vision.

Currently, less than 50% of patients achieve their targeted distance vision after treatment, even with current state-of-the-art multi-focal and other presbyopia correcting intraocular lenses, and post-cataract surgery patients should often wear glasses for reading or distance vision.

Although it is the most frequent surgical procedure in medicine, cataract surgery involves several challenges, for example: prediction of exact lens characteristics (ELP); error lens-positioning during surgery; tilt or shift during eye healing process; and change of the corneal cylinder in the elderly.

There are a few types of IOLs used to correct visual impairment, such as Mono-focal, Multi-focal and Toric (with possible combinations in the same lens). Following the installation and healing process, all kinds of IOL may move with respect to the lens capsule, thus requiring compensation by optimizing the IOL location inside the lens capsule. Typically, modification of the IOL may be needed along the optical axis of the IOL, to correct focusing problems, and/or around the optical axis of the IOL, to correct for astigmatism issues.

There are several techniques, both invasive and non-invasive, used to implement the compensations, for example:

Use of a unique UV sensitive polymer that enables compensation by post deforming of the lens. This technology requires UV isolation during the healing process and is followed by lots of inconvenience to the patient; and/or Direct modification of implanted lens shape by use of laser radiation.

Such known techniques are implemented in a surgery room environment.

U.S. Pat. No. 8,425,599 describes an accommodating intraocular lens system comprising: an optic portion comprising an anterior element and a posterior element defining an optic fluid chamber; a plurality of haptics extending radially from the optic portion, each of the plurality of haptics comprising a haptic fluid chamber in fluid communication with the optic fluid chamber, the plurality of haptics each adapted to deform in response to capsular bag reshaping, wherein each of the plurality of haptics has a maximum height dimension in an anterior-to-posterior dimension that is at least as great as a maximum height dimension of the optic portion in an anterior-to-posterior dimension; and a fluid adapted to be moved between the haptic fluid chambers and the optic fluid chamber in response to deformation of the plurality of haptics, wherein the anterior element and the posterior element are each adapted to deform in response to the fluid movement between the haptic fluid chambers and the optic fluid chamber to change the power of the intraocular lens.

U.S. Pat. No. 7,122,053 describes an accommodating intraocular lens having optical parameters that are altered in-situ using forces applied by the ciliary muscles. A lens body carries an actuator that separates two fluid-filled chambers having either the same index of diffraction or different indices of refraction. Actuation of the actuator changes the relative volumes of fluid within an optic element of the lens and alters the optical power of the lens.

U.S. Pat. No. 5,443,506 describes a variable focus intraocular lens system which alters the type of medium located between two lens surfaces of the intraocular lens system to alter the accommodation of the lens. A continuous flow path is created in the intraocular lens system which controls the flow of fluid into the optical zone of the intraocular lens. The continuous flow path contains multiple discrete segments of fluid which move through the fluid path of the lens system. The fluid segments can include segments of positively charged fluids, negatively charged fluids, air, oil, water or other fluids. The electric potential that is generated when the ciliary body contracts and relaxes is used to attract and repel certain charged fluid segments to control the type of media that is contained in the optical zone of the lens. By varying the type of media contained in the optical zone, the accommodation of the intraocular lens system can be altered. Further, by utilizing the charge generated by the contraction and relaxation of the ciliary body to move the fluid segments, no external power sources or signals are required to change the accommodation of the variable lens system of the present invention.

U.S. Pat. No. 4,816,031 discloses an IOL including a PMMA intraocular lens implant, a second soft and pliable lens disposed there over such as that of silicon, and electromechanical circuitry for regulating the distance between the soft silicon lens and the hard PMMA lens. The electromechanical circuitry can include a micro solar power cell, a microprocessor, a microfluidic pump, a micro reservoir for fluid, and a micro DC storage cell. The electromechanical circuitry provides for adjustment of the focal point of the lens system for accommodation from distance to near vision.

U.S. Pat. No. 4,932,966 discloses an accommodating intraocular lens apparatus including a lens member having a relatively flexible portion and a relatively rigid portion, with a fluid-filled chamber there between. The preferred intraocular lens also includes a hydraulic or other fluid accommodation provision for changing the shape or position of the flexible lens by changing the fluid pressure in the fluid-filled chamber in response to muscle movement of the eye.

U.S. Pat. No. 6,884,261 describes a method of preparing an accommodating intraocular lens having an optical axis for subsequent implantation. The method comprises providing an intraocular lens having first and second viewing elements interconnected by plural members. At least a portion of the members are disposed from the optical axis by a distance greater than a periphery of at least one of the viewing elements. The distance is measured orthogonal to the optical axis. The method further comprises drawing the members inwardly toward the optical axis by relatively rotating the first and second viewing elements. The method further comprises increasing the separation between the viewing elements along the optical axis while drawing the members inwardly.

U.S. Patent Publication 2016/0015511 describes an intraocular lens inserter with temperature compensation. The inserter includes an energy storage portion, an actuator portion that provides temperature compensation, and a lens support portion. The energy storage portion can include a compressible energy storage device, such as a compressible fluid, springs, and other devices. The inserter can include an actuator portion operating with a substantially incompressible fluid. The actuator can be configured to provide an operator with control over the release of pressurized fluid so as to move a plunger for the discharge of a lens from an intraocular lens cartridge, discharge of the lens being limited based at least in part on pressure feedback from the pressurized fluid due temperature increases.

U.S. Patent Publication 2016/0235587 describes a modular IOL system including intraocular primary and secondary components, which, when combined, form an intraocular optical correction device, wherein the secondary component is placed on the primary component within the perimeter of the capsulorhexis, thus avoiding the need to touch or otherwise manipulate the capsular bag. The secondary component may be manipulated, removed, and/or exchanged for a different secondary component for correction or modification of the optical result, on an intra-operative or post-operative basis, without the need to remove the primary component and without the need to manipulate the capsular bag. The primary component may have haptics extending therefrom for centration in the capsular bag, and the secondary component may exclude haptics, relying instead on attachment to the primary component for stability. Such attachment may include actuate-able interlocking members.

General Description

The present invention provides a novel technique for optimizing intraocular lens (TOL) position inside the lens capsule in a human eye at any time after the implantation and within the needed repositioning range. In one aspect, an IOL system enabling none-invasive compensation of the lens positioning inside the lens capsule, is provided. Advantageously, the invention allows for in-clinic optimization after lens implantation and wound healing without the need for another surgical invasive procedure. Further, the technique of the invention enables, if needed, removal and replacement of the IOL without the need to remove the whole support structure/cradle. In addition, the technique of the invention can be applicable with generic, off-the-shelf, lenses by mainly controlling the positioning of the generic lens inside the lens support structure/cradle, while maintaining the integrity of the lens. To compensate for such conditions as astigmatism and accommodation problems, the lens position control, according to the invention, is available for the angular and axial directions independently in order to compensate for each direction separately and the relocating of the IOL, in either direction, can be repeated as needed. The invention enables surgeons to precisely adjust the IOL based on the exact amount of visual correction and optimization needed to achieve desired vision after surgery.

To this end, the invention provides a lens support structure/holder/cradle provided with a repositioning system/mechanism/assembly utilizing mechanical displacement and adjustment of the IOL, the system includes a support structure/holder/cradle configured to hold the IOL in place and enable its spatial repositioning remotely. The support structure/holder/cradle also enables replacement of the IOL, after implantation, as the need may be. The repositioning system includes an actuator configured to be activated remotely to enable, when combined with a driving mechanism, correction of the IOL position in one or both of the angular (xy plane, theta) and axial (z) directions, i.e. rotating the IOL and changing its optical depth respectively. The actuator is configured to modify its properties, including its volume and/or three-dimensional shape, temporarily, to affect/activate the driving mechanism which in turn affects the position of the IOL in the support structure/holder. Temporal property/shape modification of the actuator can be achieved, for example, by utilizing memory shaped materials. Such memory shaped materials can deform temporarily due to changes in physical and/or environmental conditions such as the temperature. In some embodiments, the deformation includes shrinking when the memory shaped material is heated/cooled by a predetermined value/gradient. In some embodiments, the return to the original shape of the memory shaped material involves application of a spring or spring-like mechanism that forces the deformed memory shaped material to return to its original shape when the change of physical/environmental condition(s) is removed/is no longer present.

Every displacement of the IOL by the repositioning system of the invention is reversible and can be applied to rotate the IOL around its optical axis, in clockwise and/or counterclockwise directions, as well as along the optical axis, anteriorly (towards inside of the eye, i.e. closer to the retina) and/or posteriorly (far from the retina). In some embodiments, a plurality of actuators, each coupled to a respective driving mechanism, are employed, where each actuator with the coupled driving mechanism act as a ratchet being responsible for moving the IOL in one direction only (from the four directions clockwise, counterclockwise, anterior and posterior).

Thus, according to a first broad aspect of the invention, there is provided a lens support structure for supporting an intraocular lens (IOL), the lens support structure being configured and operable to be securely implanted in a human eye and hold the IOL in one of a plurality of positions, the support structure comprising a repositioning assembly configured and operable to be activated remotely by a remote energy source and controllably displace the IOL in at least one of directions along and around an optical axis of the IOL, thereby enabling moving the IOL between the plurality of positions.

In some embodiments, the repositioning assembly is configured to provide incremental transitions of said IOL between at least part of said plurality of positions.

In some embodiments, the repositioning assembly comprises at least one actuator and a respective teeth arrangement, wherein one of the actuator and the teeth arrangement has a fixed spatial relationship with the IOL, the actuator being configured and operable to selectively engage and disengage with the teeth arrangement such that when engaging a relative incremental movement occurs between the actuator and the teeth arrangement, resulting in said controllable displacement of the IOL between two adjacent positions of said plurality of positions. The actuator and/or respective teeth arrangement may define a ratchet mechanism such that said relative incremental movement occurs in only one direction in each of said at least one of directions along and around the optical axis of the IOL. The actuator may be reversibly shiftable between a first and second spatial configurations thereby respectively providing said engagement and disengagement with said teeth arrangement. The actuator may comprise a modifiable element formed by a memory shaped material configured and operable to provide at least said first spatial configuration of the actuator when said repositioning assembly is remotely activated by said remote energy source. The actuator may comprise a spring-like element coupled to said modifiable element and being configured and operable to provide at least said second spatial configuration of the actuator when said repositioning assembly is not activated by said remote energy source. The modifiable element may comprise nitinol.

In some embodiments, the remote energy source is configured and operable to provide heat to at least part of said repositioning assembly.

In some embodiments, the remote energy source comprises a radiating element.

In some embodiments, the remote energy source comprises a laser source.

In some embodiments, the remote energy source comprises an electromagnetic radiation transmitter and said repositioning assembly comprises an electromagnetic radiation receiver.

In some embodiments, the repositioning assembly comprises at least one pair of said actuator, each actuator being configured and operable to controllably displace the IOL in one of opposite directions either around or along the optical axis of the IOL. The repositioning assembly may comprise a pair of said teeth arrangement, each teeth arrangement interacts with one of said actuators of the pair, to thereby enable displacement of the IOL in opposite directions around the optical axis of the IOL. The repositioning assembly may comprise one teeth arrangement that interacts with said actuators of the pair, to thereby enable displacement of the IOL in opposite directions along the optical axis of the IOL.

In some embodiments, the lens support structure further comprises a fibrosis protector configured and operable to seal the repositioning assembly and prevent tissue invasion to the repositioning assembly while enabling user inspection and activation of the repositioning assembly.

According to another aspect of the invention, there is provided a lens control system for controlling position of an intraocular lens, the lens control system comprising the lens support structure and a remote source energy configured and operable to remotely activate said repositioning assembly. In some embodiments, the energy source comprises at least one of the following: a heat generator, a laser beam generator and an electromagnetic radiation transceiver.

According to another aspect of the invention, there is provided an intraocular lens (IOL) system comprising the lens support structure and an IOL integrally mounted in the lens support structure.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIGS. 3a to 3d2 schematically illustrate a non-limiting example of a repositioning assembly for angular and axial compensations.

DETAILED DESCRIPTION OF EMBODIMENTS

As described above, the present invention is aimed at providing an intraocular lens (TOL) support structure/cradle enabling remote (non-invasive) controlled adjustment of the lens' position either along the optical axis of the IOL (the Z direction) or around the optical axis of the IOL (the Theta direction), or both Z (axial) and Theta (angular) directions. To this end, the invention provides a remotely controlled repositioning assembly incorporated in the IOL's support structure.

Figure 1A:
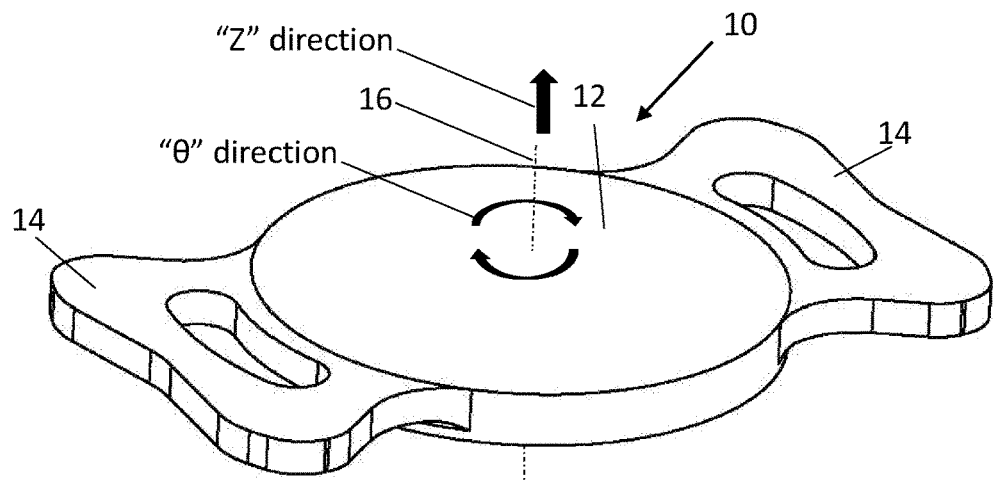
FIG. 1a shows a typical shape of an IOL and defines the directions for compensation when required.

Reference is made to FIGS. 1a-1h, schematically illustrating the general principles of the technique of the present invention. FIG. 1a generally shows a typical, commercially available, IOL implant 10. The IOL implant 10 includes the IOL 12 (the optically active part), and one example of haptics 14, attached to the circular IOL 12 (the haptics can be removably attached to the lens body or may together form one integral part) to support safe implantation of the IOL in a human eye. The IOL is typically implanted in the anatomical lens capsule compartment, or in the anatomical sulcus in case the lens capsule is damaged/ruptured, and the haptics 14 may be costumed to the specific implantation anatomical site. Herein below, the lens capsule and sulcus can be interchangeably used to indicate the implantation site. Also shown in the figure are the possibly required movements/adjustments to be provided to the IOL 12 after implantation to provide the required correction(s) to the user's vision. As illustrated, the main movements applied to the IOL are in the axial direction along direction Z, which is along the Optical axis 16 of the IOL 12, and in the angular direction of angle Theta (θ), which is around the optical axis 16.

Figure 1B:
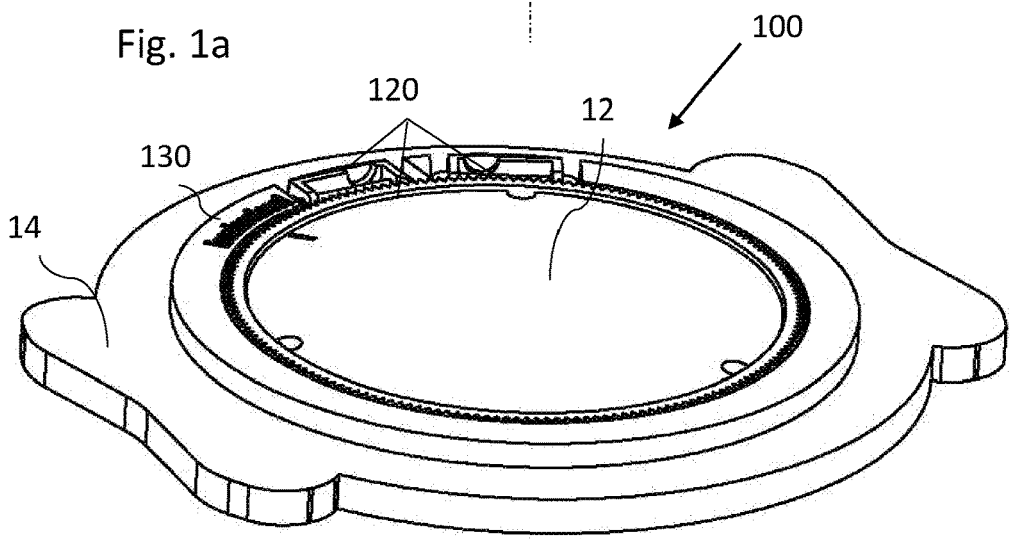
FIG. 1b schematically illustrates an isometric view of an embodiment of a lens support structure enabling for angular compensation.
Figure 1C:
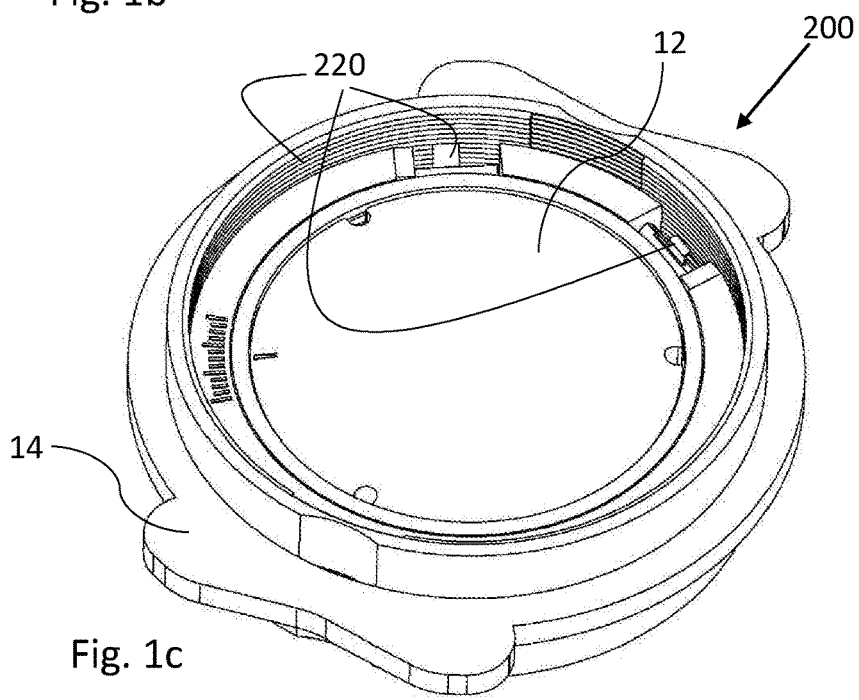
FIG. 1c schematically illustrates an isometric view of an embodiment of a lens support structure enabling for axial compensation.
Figure 1D:
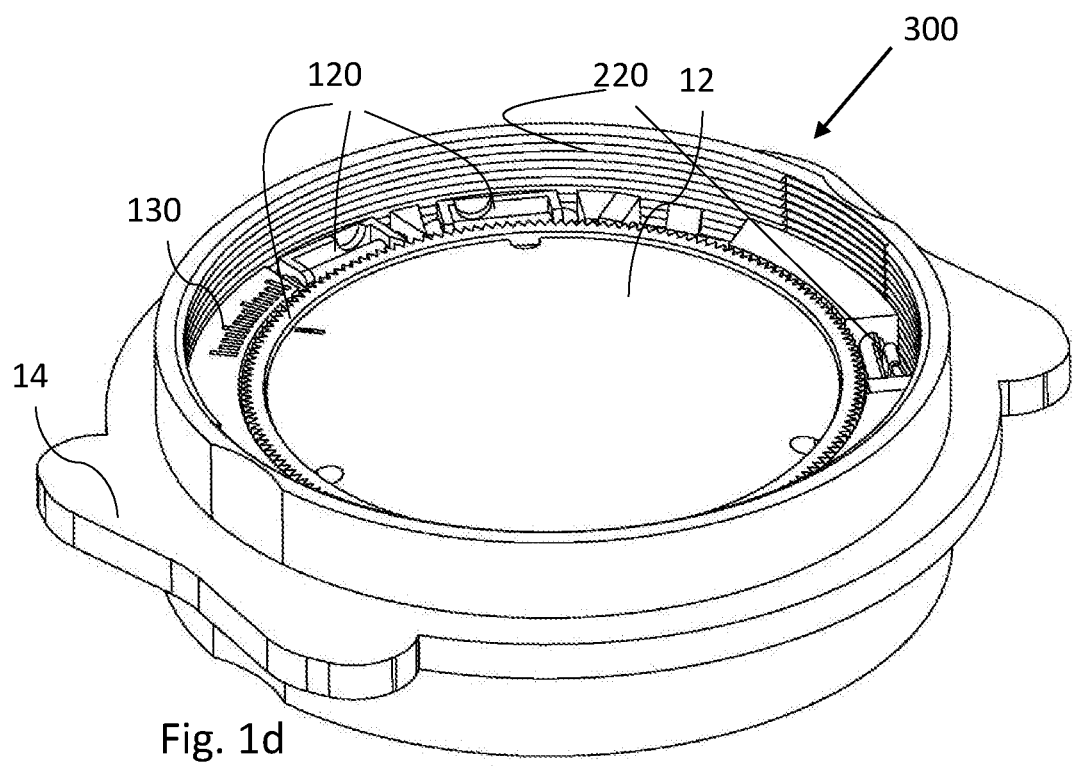
FIG. 1d schematically illustrates an isometric view of an embodiment of a lens support structure enabling for both angular and axial compensations.

Each one of FIGS. 1b, 1c and 1d shows an isometric view of a non-limiting example of a lens support structure enabling for compensation and vision correction by enabling non-invasive angular (Theta) and/or axial (Z) displacement of the IOL while being already implanted in the lens capsule of the human eye. Accordingly, FIGS. 1b to 1d show lens support structures, 100, 200 and 300, for supporting an IOL 12, the lens support structures being configured and operable to be securely implanted in a lens capsule of a human eye (as shown further below) and hold the IOL in one of a plurality of positions, either with an angular position with respect to an optical axis of the IOL, or in an axial position with respect to the optical axis of the IOL, or in both angular and axial positions. As will be further detailed below, each support structure includes at least one repositioning assembly, such as 120 and 220, configured and operable to be activated remotely by a remote energy source (as shown in FIG. 1f) and controllably displace the IOL in at least one of directions along and around the optical axis of the IOL (shown in FIG. 1a), thereby enabling moving the IOL between the plurality of positions. It should be understood that unless the repositioning assembly is activated, the IOL is safely and stably located within the lens capsule. The lens support structure is configured to hold the IOL in a permanent position/orientation in both the angular and axial directions until the repositioning assembly is activated to displace the IOL in one or more of the two directions. However, as mentioned above, the lens support structure of the invention is also configured to enable removal and substitution of the IOL if needed.

It is noted that for the simplicity of presentation, the example in FIG. 1b relates to the ability of the technique of the present invention to displace the IOL in the angular direction, around the IOL's optical axis, thus includes the repositioning assembly 120; the example in FIG. 1c relates to the ability of the technique of the present invention to displace the IOL in the axial direction, along the IOL's optical axis, thus includes the repositioning assembly 220, and the example in FIG. 1d relates to the ability of the technique of the present invention to displace the IOL both in the angular and axial directions, around and along the IOL's optical axis, yet in each direction independently, thus includes both repositioning assemblies 120 and 220 respectively.

The technique of the present invention advantageously enables accurate and precise displacement of the IOL after it has been implanted, for example down to resolutions of less than a millimeter and less than 1 angle. In some non-limiting examples, the linear, axial displacement pitch can be from 0.15 mm to 0.5 mm extending over total linear displacement range of about 4 mm. In some non-limiting examples, the angular displacement pitch can be from 0.25 degree to 1 degree extending over total angular displacement range of about 20 degrees. As such, the lens support structure may be provided with scale marks 130 that help the treating doctor in identifying the exact angular and/or axial position (both old and new, before and after displacement) of the IOL. The repositioning assembly (120, 220) is configured and operable to provide incremental transitions of the IOL between at least part of the plurality of positions in which the IOL can be located. In the shown examples, only scale marks of the angular repositioning assembly 120 are shown, however, it is appreciated that scale marks or any other known technique can be applied also to the linear, axial, repositioning assembly 220. It is appreciated that each two adjacent positions of the plurality of available positions for the IOL in the support structure can be distanced from each other in equal, constant, distances/pitches/steps, or can be distanced from each other in different, variable, distances/pitches/steps.

Figure 1E:
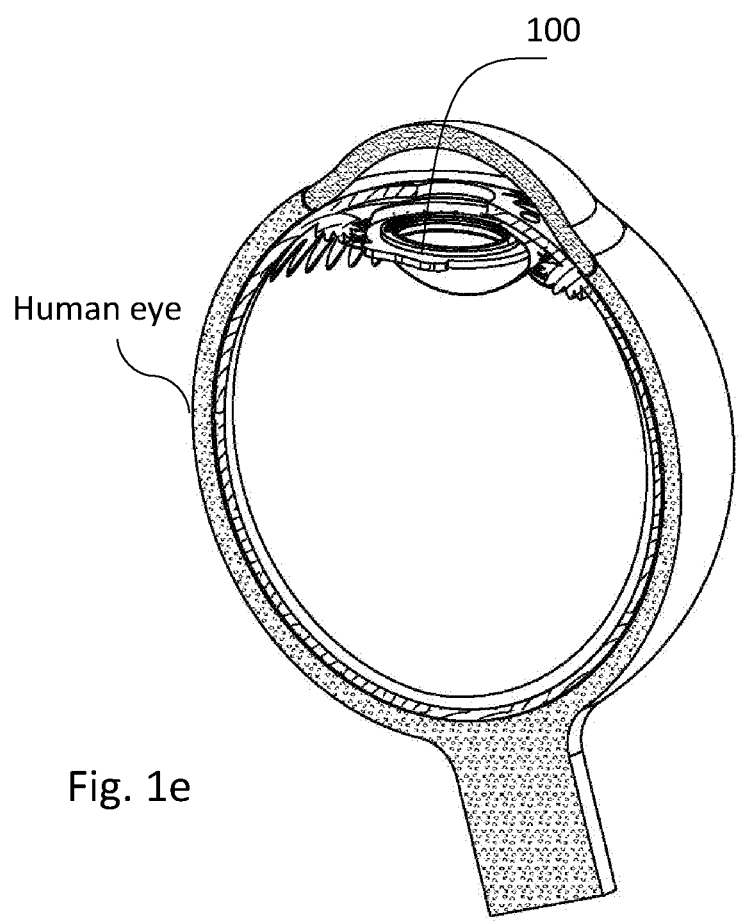
FIG. 1e to 1h show examples of the lens support structures of the invention as implemented in a human eye, and the application of energy.
Figure 1F:
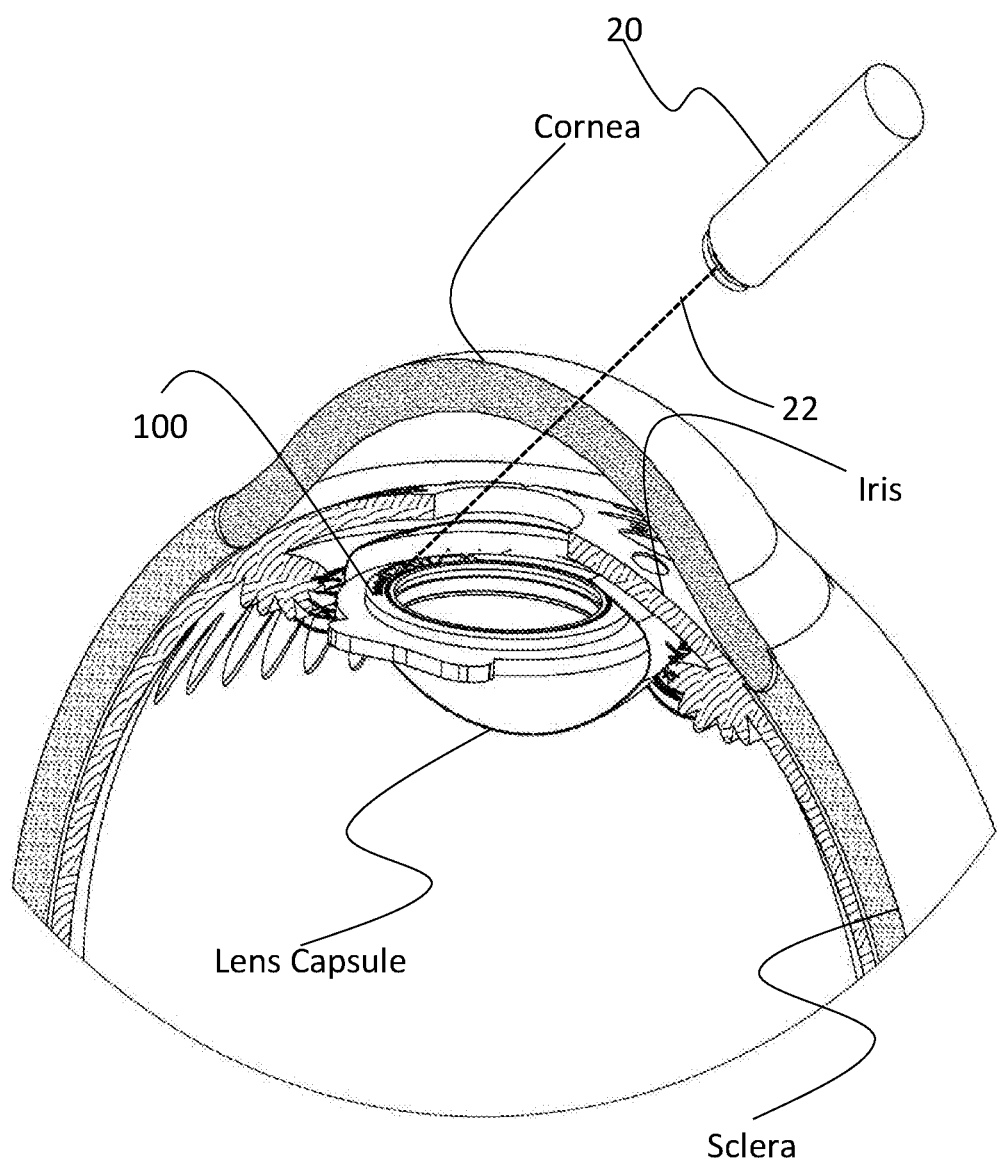
Figure 1G:
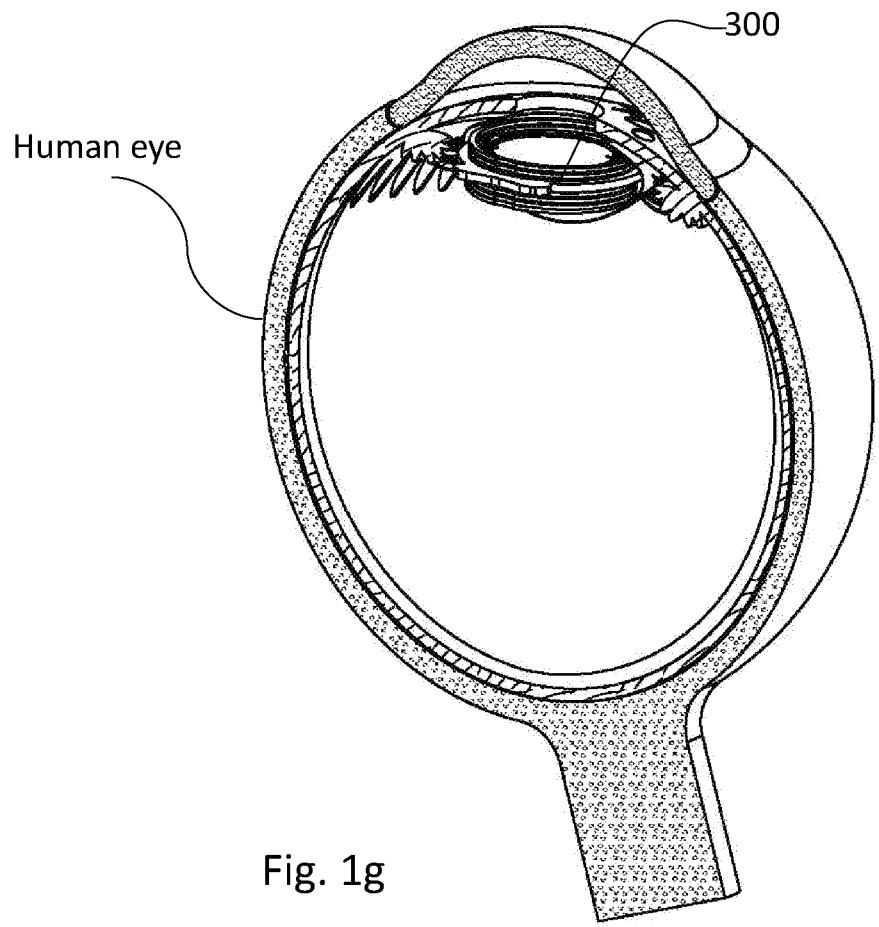
Figure 1H:
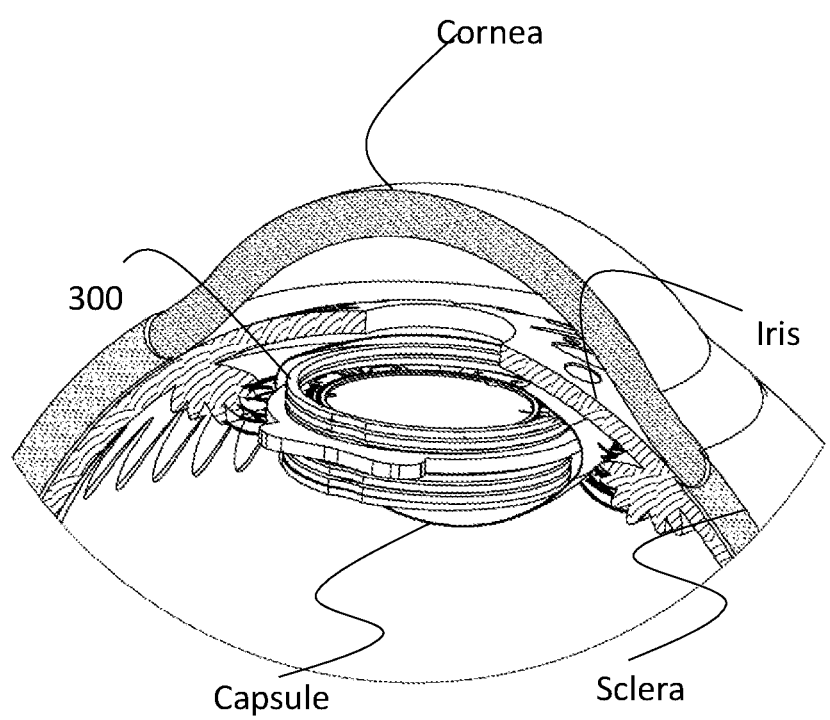

FIGS. 1e and 1g show non-limiting examples of implementation of the lens support structures of FIGS. 1b and 1d, respectively, inside the human eye, providing among other issues the impression of size of such lens support structures in relation to the human eye. Consistently, FIG. 1f is a close-up view of FIG. 1e, and FIG. 1h is a close-up view of FIG. 1g, showing the lens support structures surrounded by the different anatomical parts of the human eye, such as the lens capsule, the iris, the sclera and the cornea that are arranged from inside the eye to the outside. FIG. 1f further schematically illustrates the usage of a remote energy source 20 that produces energy 22 to remotely activate relevant parts of the repositioning assembly in the lens support structure. In some embodiments, the energy source requires direct visual line/uninterrupted route/line of sight between the energy source and the part being remotely activated, while in some other embodiments, there is no such requirement and the activation can be achieved without direct visual line. In some embodiments, as will be detailed further below, the energy source is configured to provide energy in the form of heat to thereby cause activation of relevant parts of the repositioning assembly. For example, heat can be applied by using an energy source in the form of a laser beam generator configured to irradiate relevant parts of the repositioning assembly to heat them and result in a predetermined temperature increase to thereby activate them and cause the desired displacement of the IOL. In another example, the energy source includes an electromagnetic transceiver configured and operable to generate a radiation field, such that the receiver part, e.g. a micro-antenna, is located in the vicinity of the relevant parts of the repositioning assembly, to thereby heat and activate them.

Figure 2A:
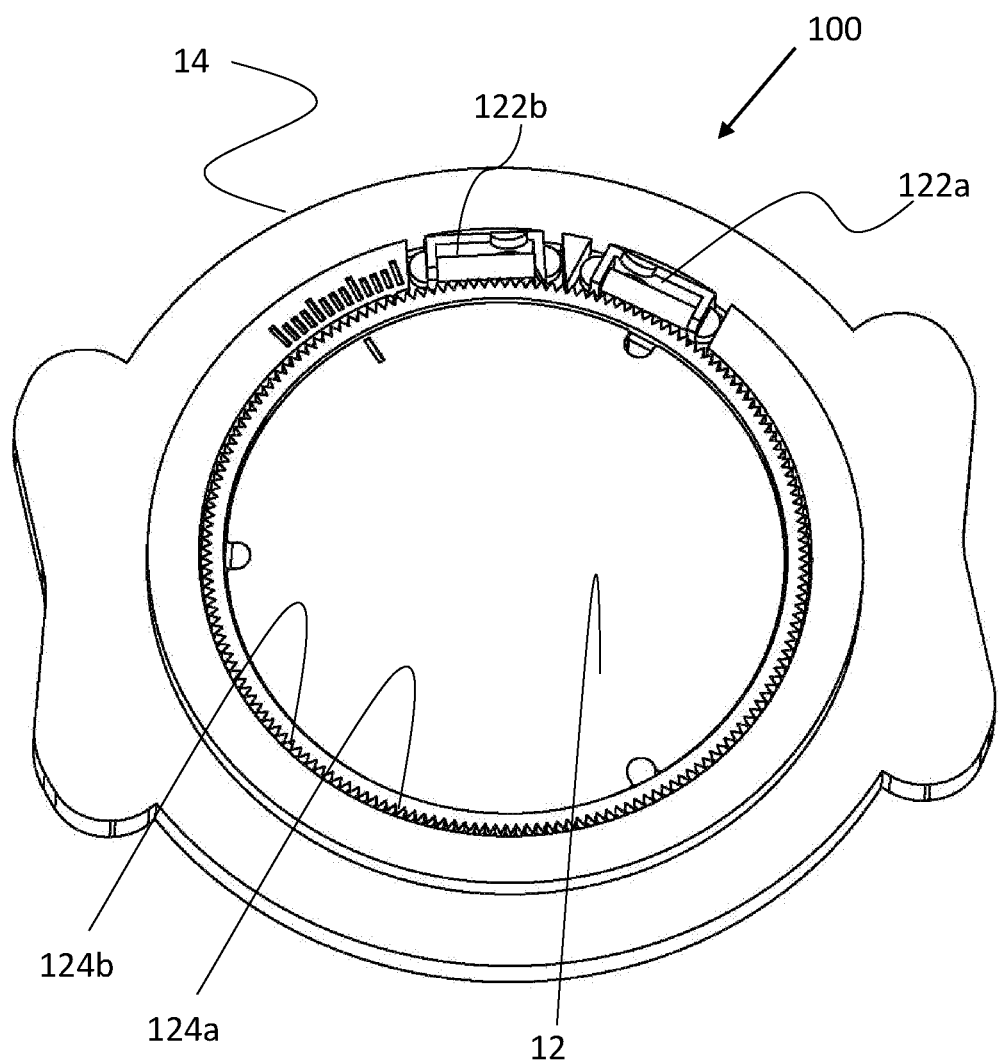
FIGS. 2a to 2f2 schematically illustrate a non-limiting example of a repositioning assembly for angular compensation.

Reference is now made to FIGS. 2a to 2f2 that more specifically exemplify the non-limiting example of the lens support structure 100 with the repositioning assembly 120 that enable lens' incremental movement/displacement for angular (Theta) compensation around the optical axis of the IOL. FIG. 2a shows the lens support structure 100 in a view from above; FIG. 2b shows the lens support structure 100 in an exploded view; FIGS. 2c and 2d show close-up views of the repositioning assembly 120. As shown in FIG. 2a, the IOL 12 is located in the haptics housing 14 which is securely received in the lens capsule of the eye.

Figure 2B:
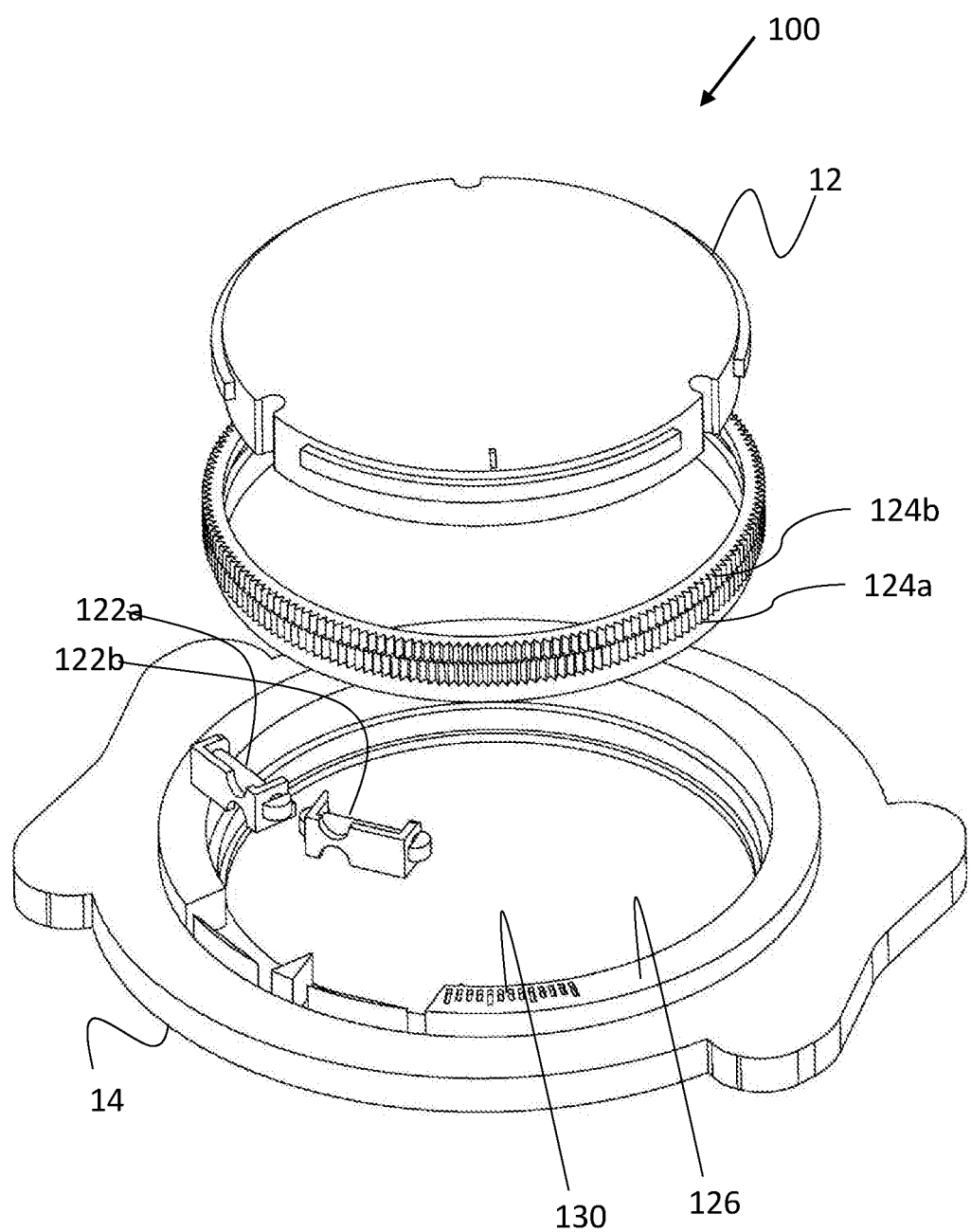
Figure 2C:
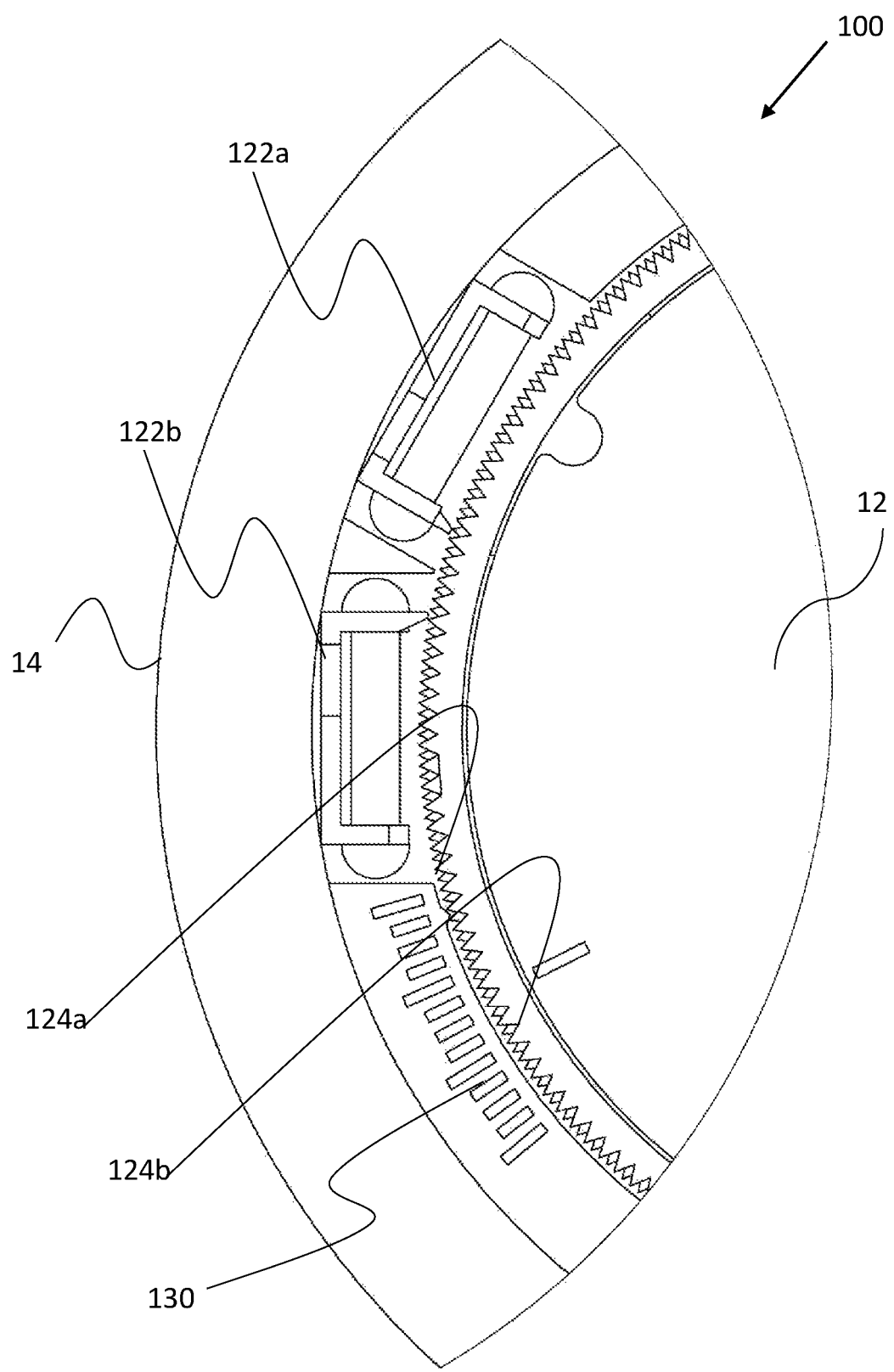
Figure 2D:
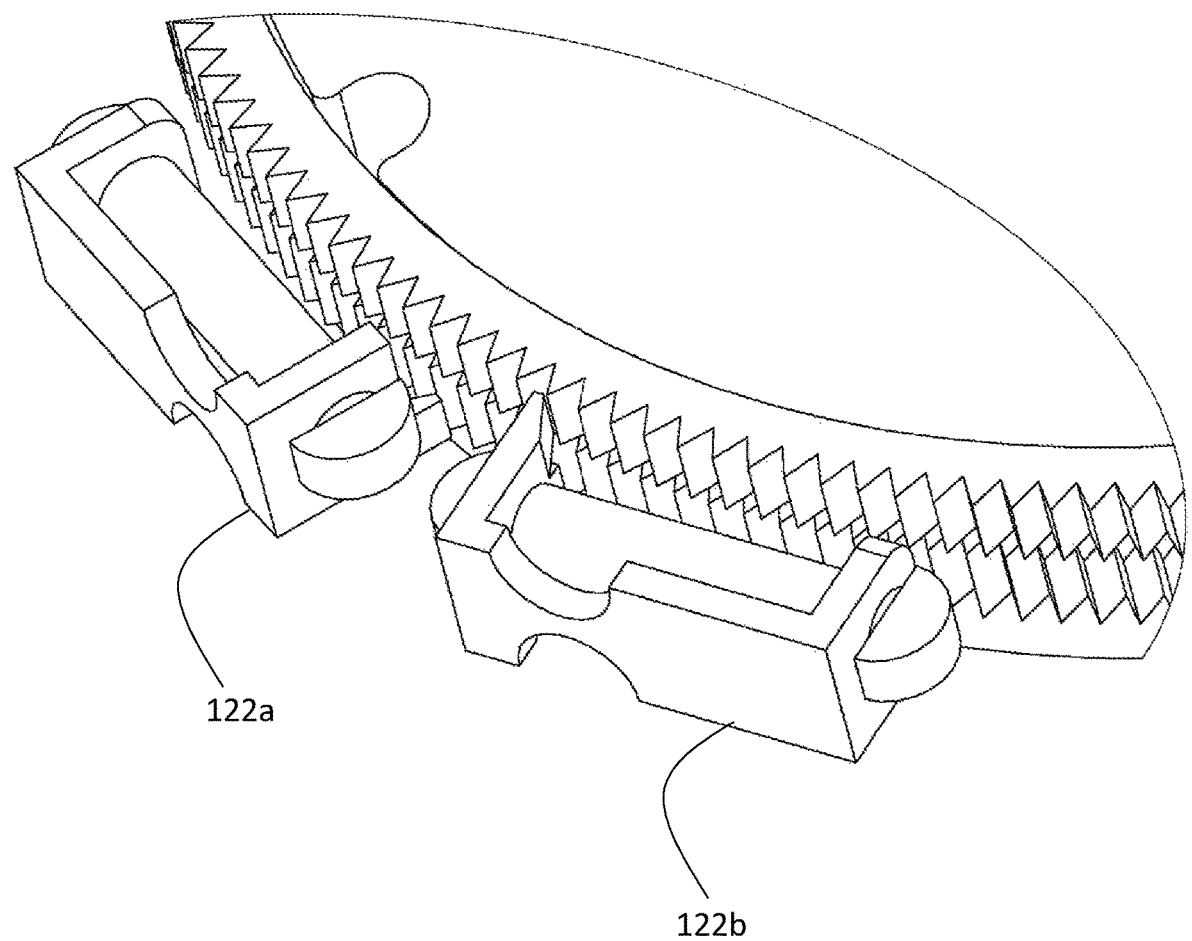

The repositioning assembly 120 includes at least two elements responsible for the displacement of the IOL: an actuator 122a and a teeth arrangement (step driving mechanism) 124a associated with the actuator. In some embodiments, the repositioning assembly includes more than one actuator with their respective associated teeth arrangements. In the described example, a pair of (two) actuators 122a and 122b together with a pair of (two) associated teeth arrangements are shown (in FIG. 2d it is shown in assembled form). As shown in FIG. 2b, the actuators 122a and 122b are safely housed in an actuator housing 126 which is received between the teeth arrangement and the haptics housing 14. Each of the actuators, 122a and 122b, and the associated teeth arrangement, 124a and 124b respectively, acts to move the IOL in one direction around the optical axis of the IOL. In other words, the pairs of actuators and associated teeth arrangements enable movements of the IOL in opposite directions. More specifically, one actuator with its associated teeth arrangement acts to move the IOL in a clockwise direction while the other actuator with its associated teeth arrangement acts to move the IOL in counterclockwise direction. It should be noted that it can be the case that each of the teeth arrangements or pair of actuator and teeth arrangement is designed to allow movement of the IOL in one of the aforementioned directions while preventing the movement of the IOL in the opposite direction. In some examples, the oppositely oriented teeth arrangements form a ratchet mechanism which is split into two sections (each section is formed by one of the teeth arrangements) with half pitch difference there between (as shown for example in FIG. 2c), to thereby enable high increment resolution while keeping a reasonable structural size.

Either the actuator or the teeth arrangement has a fixed spatial relationship with the IOL, such that it moves together with the IOL. In the described example, the teeth arrangement is attached to the IOL and both move together with respect to the actuator. Specifically, the teeth arrangements 124a and 124b are configured with circular shapes surrounding the IOL from their inner side and with the teeth pointing outwardly towards the haptics housing 14 where the actuators 122a and 122b are located. As appreciated, each of the teeth arrangements 124a and 124b forms a spur gear structure.

Each one of the actuators 122a and 122b is configured and operable to selectively engage and disengage with the associated teeth arrangement, 124a and 124b respectively, such that when engaging a relative incremental movement occurs between the actuator and the associated teeth arrangement, resulting in the controllable displacement of the IOL (because of its adherence to the teeth arrangements) between two adjacent positions of the plurality of positions in which it can reside.

Specific non-limiting configurations of the actuators 122a and 122b are shown in FIGS. 2e1-2f2. As illustrated, the actuator 122a or 122b is reversibly shift-able between a first and second spatial configurations, the first configuration 1221, when the energy source is/isn't acting on the actuator, is shown in FIGS. 2f1 (side view) and 2f2 (isometric view), and the second configuration 1222, resulting from the energy source isn't/is acting on the actuator, is shown in FIGS. 2e1 (side view) and 2e2 (isometric view). The shift of the actuator between the two configuration provides that the actuator engages in one of the configurations with the teeth arrangement to cause movement of the teeth arrangement and the IOL attached to it, and disengages in the other configuration (e.g. the one shown in FIGS. 2e1 and 2e2) from said teeth arrangement to thereby keep the IOL safely positioned in one of the available plurality of positions.

In some embodiments, the actuator 122 includes a modifiable element 1224 configured and operable to provide at least one of the first and second spatial configurations, 1221 and 1222, of the actuator. The modifiable element 1224 changes its configuration as a result of application of energy or lack or application of energy. In some embodiments, the modifiable element 1224 is formed by a memory shaped material. Memory shaped materials are materials that can have certain spatial configuration(s) under predetermined condition(s). For example, in some embodiments, the invention utilizes Nitinol (Nickel Titanium alloy) as a memory shaped material for use in the modifiable element 1224 of the actuator.

As appreciated, Nitinol is configured to change its structure from martensitic phase to austenite under gradient of a few Celsius degrees. At the temperature conditions of about 32-37° C. Nitinol is in martensitic phase being fictile and can be shaped to a desired shape under external forces. On the other side, raising the temperature to 41-43° C. causes phase transition into austenite where Nitinol changes its shape (deforms) to take a shape saved in its "memory" even while under certain amount of external forces, e.g. forming the first spatial configuration of the actuator when engaging with the teeth arrangement. Once the temperature returns back to about 37° C., the nitinol returns back to its fictile state and can be reshaped as desired, thus forming the second spatial configuration of the actuator.

Incorporating such a reciprocating mechanism with ratchet mechanism, as described above, may be used to generate incremental movement steps in one direction. Combining more than one actuator enables to move back and forth on each direction.

In some embodiments, the actuator includes a spring-like element 1226 coupled to the modifiable element 1224 and being configured and operable to provide or at least support the actuator in taking at least the other spatial configuration between the first and second spatial configurations of the actuator.

In this specific but not limiting example, the spring-like element 1226 is formed as an elastic bracket 1228 in "U" shape, though it should be understood that the invention is not limited to this specific configuration and the bracket can be shaped other way, as well as such spring-like mechanism may have other suitable configurations. Such U-shaped bracket 1228, is formed by a base side 1228a and side walls 1228b. The bracket 1228 is asymmetric, as shown in the figures a latch 1228c exist only on one side wall. The base side 1228a actually function like a spring. When the nitinol wire 1224 (the memory shaped element) absorbs enough heat from the remote energy source, it shrinks and causes a lateral movement of the latch 1228c and the actuator deforms, as shown in FIGS. 2f1 and 2f2. The latch 1228c pushes the tooth close to it on the teeth arrangement and forces the teeth arrangement to turn. While turning occurs, the other actuator of the pair acts like a No-Back braking element, preventing the teeth arrangement from the reverse turning, at the time when the heat dissipates and the Nitinol can expand, such that the bracket forces the Nitinol and the actuator to return to the other configuration (as in FIGS. 2e1 and 2e2).

Figure 3A:
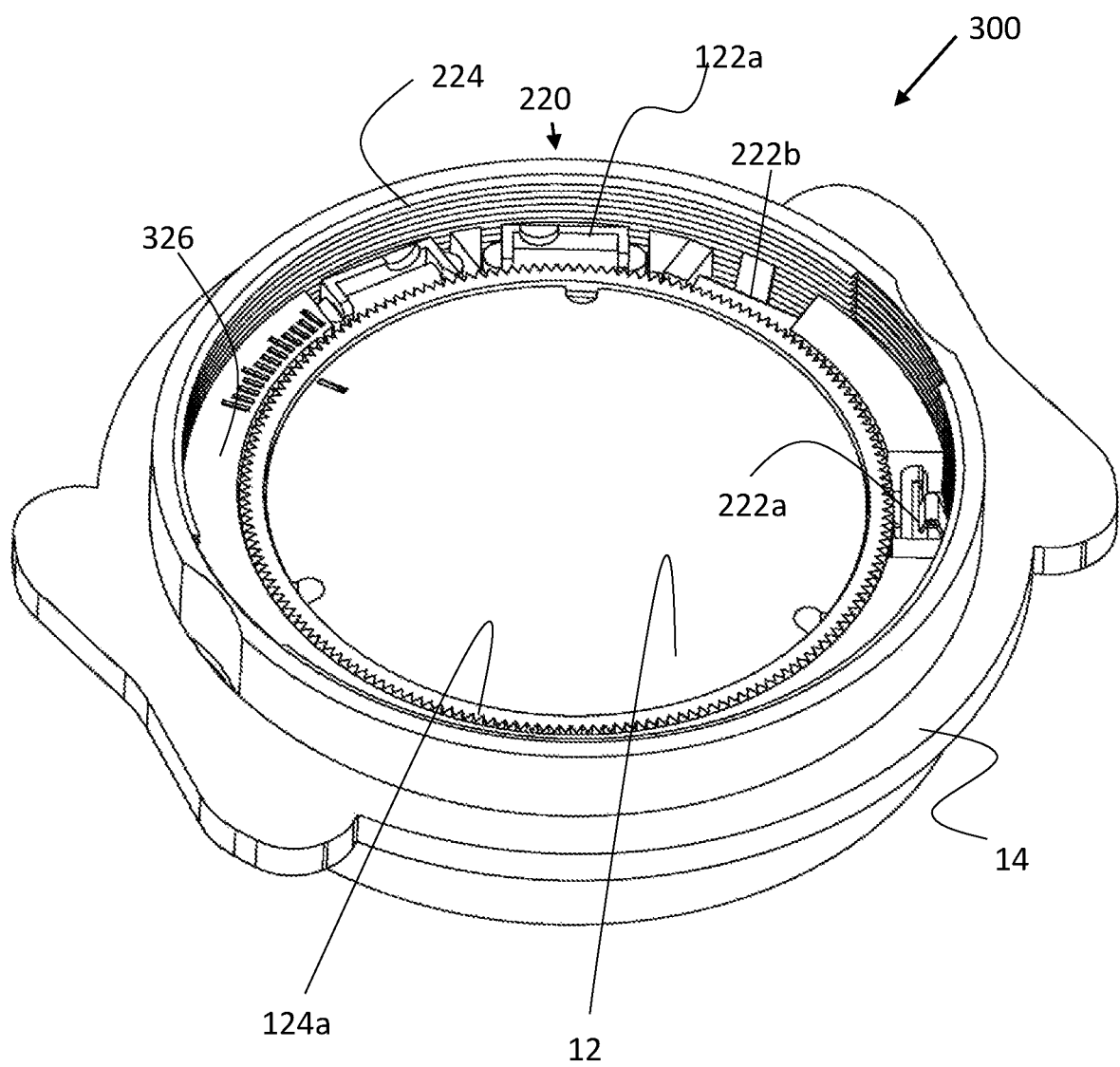
Figure 3B:
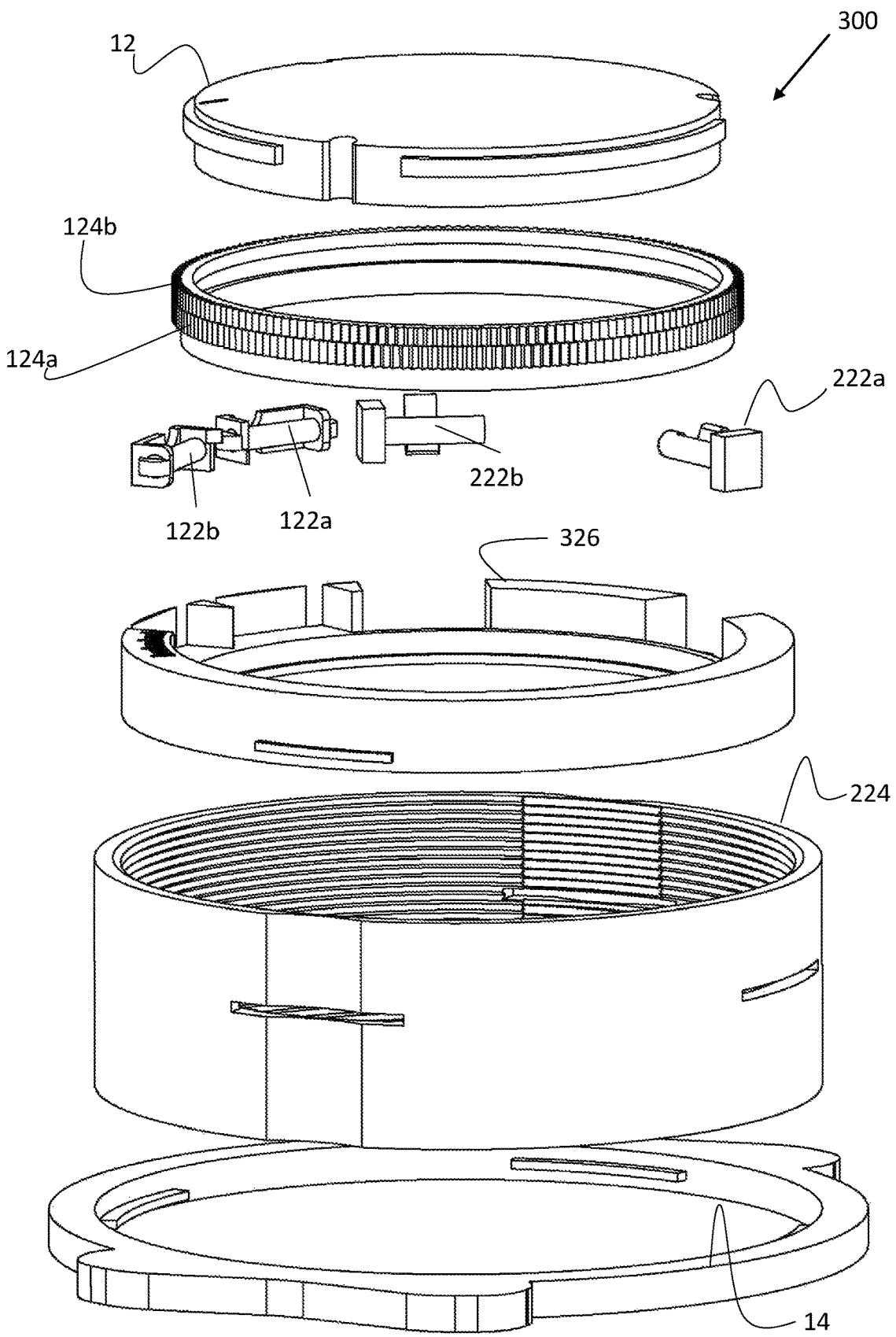

Reference is now made to FIGS. 3a to 3d2 that more specifically exemplify the non-limiting example of the lens support structure 300 with the repositioning assemblies 120 (as explained above) and 220 that enable lens' incremental movement/displacement for angular (Theta) compensation around the optical axis of the IOL and for axial (Z) compensation along the optical axis of the IOL. It should be noted again that the compensation, by movements, is independent in each of the angular and axial directions. FIG. 3a shows the lens support structure 300 in a view from above and FIG. 3b shows the lens support structure 300 in an exploded view. As shown in FIG. 3a, the IOL 12 is located in the haptics housing 14 which is securely received in the lens capsule of the eye.

The repositioning assembly 220 includes at least two elements responsible for the axial displacement of the IOL: an actuator 222a and a teeth arrangement (step driving mechanism) 224 in the axial, Z, direction and associated with the actuator. In some embodiments, the repositioning assembly includes more than one actuator associated with the teeth arrangement 224. In the described example, a pair of (two) actuators 222a and 222b are shown. As shown in FIGS. 3a and 3b, all the actuators 122a, 122b, 222a and 222b are safely housed in an actuator housing 326 which is received by the haptics housing 14. Each of the actuators 222a and 222b with the associated common teeth arrangement 224 acts to move the IOL in one direction along the optical axis of the IOL. In other words, the pair of actuators and associated teeth arrangement enable movements of the IOL in opposite directions. More specifically, one actuator with the associated common teeth arrangement acts to move the IOL in an anterior direction, towards the inside of the eye, while the other actuator with the associated common teeth arrangement acts to move the IOL in a posterior direction, towards outside the eye. It should be noted that it can be the case that each actuator of the pair is designed to allow movement of the IOL in one of the aforementioned directions while preventing the movement of the IOL in the opposite direction.

Either the actuator or the teeth arrangement have a fixed spatial relationship with the IOL, such that it moves together with the IOL. In the described example, the actuator is attached to the IOL and both move together with respect to the teeth arrangement.

It is noted that the actuators 222a and 222b have identical configurations but are positioned inversely with respect to the teeth arrangement 224 such that one moves upwardly with respect to the teeth arrangement and the other moves downwardly with respect to the teeth arrangement.

Each one of the actuators 222a and 222b is configured and operable to selectively engage and disengage with the common teeth arrangement, such that when engaging a relative incremental movement occurs between the actuator and the teeth arrangement, resulting in the controllable displacement of the IOL (because of its adherence to the actuators) between two adjacent positions of the plurality of positions in which it can reside.

Specific non-limiting configurations of the actuators 222a and 222b are shown in FIGS. 3c1-3d2. As illustrated, the actuator 222a or 222b is reversibly shiftable between a first and second spatial configurations, the first configuration 2221, when the energy source is/isn't acting on the actuator, is shown in FIGS. 3c2 (isometric view) and 3d2 (side view), and the second configuration 2222, resulting from the energy source isn't/is acting on the actuator, is shown in FIG. 3c1 (isometric view) and 3d1 (side view). The shift of the actuator between the two configuration provides that the actuator engages in one of the configurations with the teeth arrangement to cause movement of the actuator and the IOL attached to it, and disengages in the other configuration (e.g. the one shown in FIG. 3d1) from the teeth arrangement to thereby keep the IOL safely positioned in one of the available plurality of positions.

In some embodiments, the actuator 222 includes a modifiable element 2224 configured and operable to provide at least one of the first and second spatial configurations, 2221 and 2222, of the actuator. The modifiable element 2224 changes its configuration as a result of application of energy or lack or application of energy. In some embodiments, the modifiable element 2224 is formed by a memory shaped material, such as nitinol.

At the temperature conditions of about 32-37° C. Nitinol is in martensitic phase, while raising the temperature to 41-43° C. causes phase transition into austenite where Nitinol deforms into its memory shape, e.g. forming the first spatial configuration (deformed configuration) of the actuator. Once the temperature returns back to about 37° C., the nitinol relaxes, thus forming the second spatial configuration of the actuator. In the specific example described, the modifiable element 2224 transforms its three dimensional shape by twisting/turning around its longitudinal axis x. the modifiable element 2224 is attached fixedly at one side 2224b to a stable platform 2225 and at the other side it is free. Therefore, when the modifiable element deforms it twists towards its free end 2224a around its axis x because, as will be further described below, the modifiable element is held by a bracket that prevents or at least minimizes any deformation along the axis x.

Incorporating such a reciprocating mechanism with ratchet mechanism, as described above, may be used to generate incremental movement steps in one direction. Combining more than one actuator enables to move up and down on each direction.

In some embodiments, the actuator includes a spring-like element 2226 coupled to the modifiable element 2224 and being configured and operable to provide or at least support the actuator in taking at least the other spatial configuration between the first and second spatial configurations of the actuator. In this case, the spring-like element 2226, as described above, enables the modifiable element to deform around the longitudinal axis x while prevents/minimizes deformation along the axis x.

In this specific but not limiting example, the spring-like element 2226 is formed as an elastic semi-cylindrical bracket, though it should be understood that the invention is not limited to this specific configuration and the bracket can be shaped other way, as well as such spring-like mechanism may have other suitable configurations. A latch 2228 is attached to the element 2226 such that it moves together with it. When the nitinol wire 2224 (the memory shaped element) absorbs enough heat from the remote energy source, it deforms and twists in counterclockwise direction as shown in FIG. 3c2. As the element 2226 is attached to the element 2224, the element 2226 and the latch 2228 also turn in a counterclockwise direction. The latch goes down and pushes the tooth close to it on the teeth arrangement 224 and forces the actuator housing 226 and the IOL attached thereto to go up as the latch pushes down on the teeth arrangement which is fixed in place inside the lens capsule. The other actuator of the pair (responsible for pushing on the teeth upwardly to cause itself go downwardly) may act like a No-Back braking element, preventing the IOL from going down, at the time when the heat dissipates.

In the example described in FIGS. 3d1 and 3d2 showing the interaction of the actuator with the teeth arrangement, the described configuration is the one where the actuator pushes up on the teeth arrangement causing the actuator and the IOL to go down for one step. The relaxed configuration is shown in FIG. 3d1 while the activated configuration is shown in FIG. 3d2.

While not specifically illustrated, it is appreciated that the above explanations with respect to the lens support structure 300 are also valid to the lens support structure 200, as shown in FIG. 1c, with at least the following exceptions: the actuator housing in the lens support structure 200 is configured to house the actuators of the repositioning assembly 220 only, and the IOL 12 has no limitation in the angular direction and can be either configured to turn freely in the angular axis (e.g. if the IOL is mono-focal) or can be fixed at a specific orientation in the angular axis.

The lens support structure of the invention (100, 200 and 300) is an implant that is implanted inside a living tissue, i.e. inside the lens capsule or the sulcus of an eye. As known, the living body reacts to foreign materials. One of the reactions is Fibrosis which is the formation of excess fibrous connective tissue in an organ or tissue in a reparative or reactive process. Tissue formation can interrupt with and block the repositioning assemblies 120 and 220 and prevent their activation or normal action.

Figure 4A:
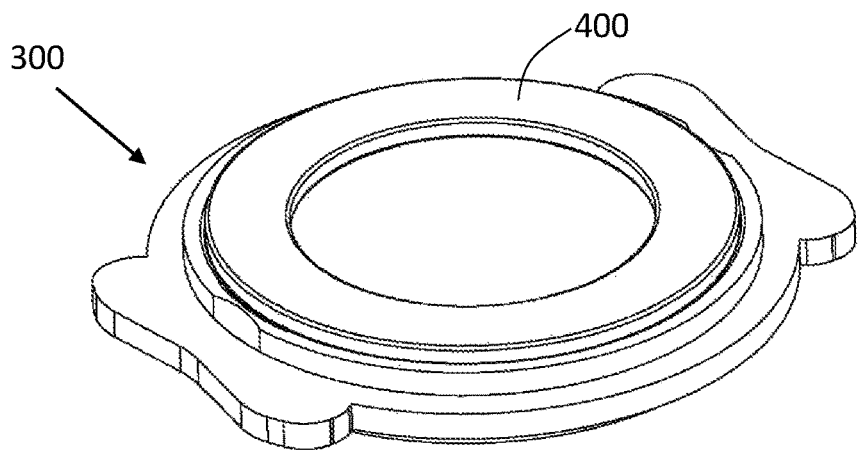
FIGS. 4a and 4b schematically illustrate a non-limiting example of a fibrosis protector for use in a lens support structure of the invention.
Figure 4B:
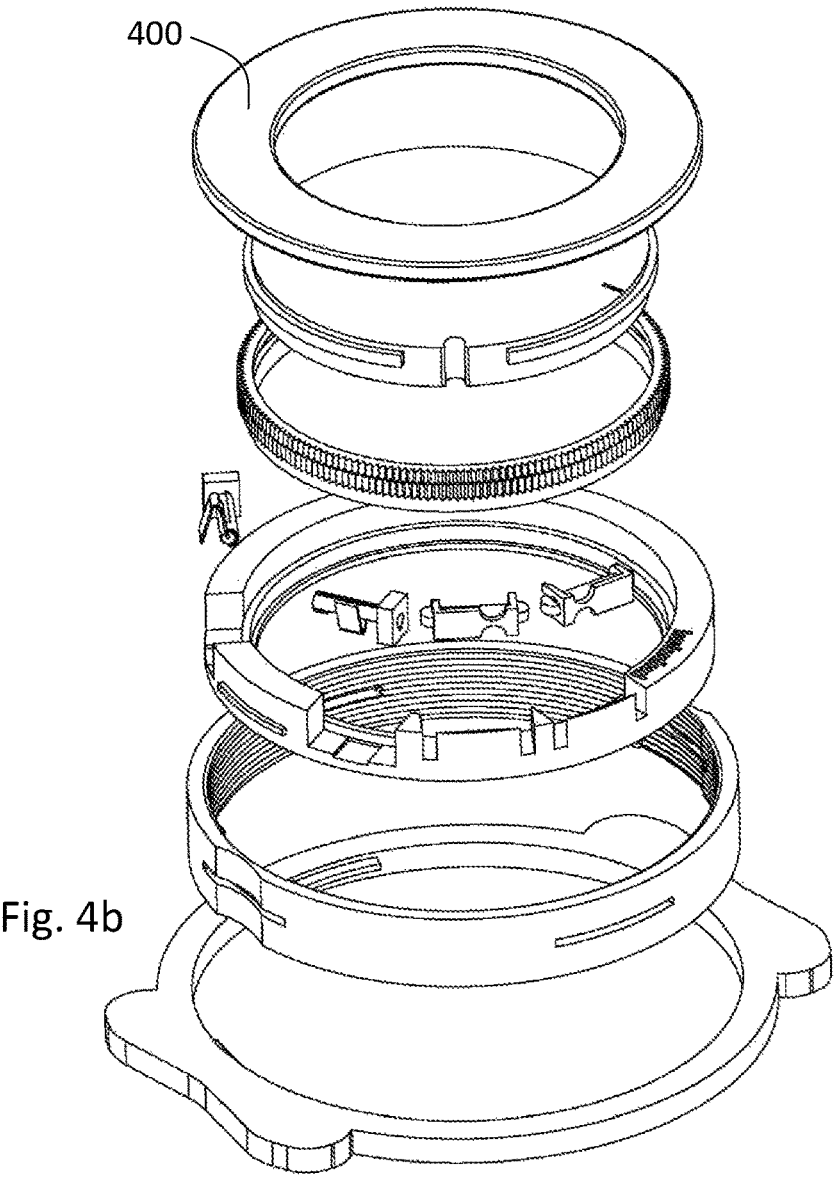

Reference is now made to FIGS. 4a-4b illustrating a fibrosis protector 400 configured to be used with any of the lens support structures of the present invention. In the non-limiting example shown, the fibrosis protector 400 is exemplified with the lens support structure 300 shown in FIG. 4a in its assembled configuration and in FIG. 4b in an exploded view. The fibrosis protector 400 has a ring shape configured to match the lens support structure such that it seals/covers the repositioning assembly and specifically the actuators and the associated teeth arrangement. The fibrosis protector 400 is preferably configured with sharp edges providing discontinuity for the cells thus inhibiting or at least minimizing their progress and preventing their invasion into the repositioning assembly. The fibrosis protector 400 is made from a transparent material to enable inspection of the repositioning assembly and proper activation of the actuators by the external energy source.

The invention claimed is:

1. A lens support structure for supporting an intraocular lens (IOL), the lens support structure being configured and operable to be securely implanted in a lens capsule of a human eye and hold the IOL in one position out of a plurality of positions, the lens support structure comprising:
a lens repositioning assembly configured and operable to be activated remotely by a remote energy source and controllably and independently displace the IOL in at least one of axial or angular directions, respectively along or around an optical axis of the IOL, thereby enabling moving the IOL between the plurality of positions, the repositioning assembly comprises at least one actuator and at least one teeth arrangement facing each other, wherein one of the at least one actuator and the at least one teeth arrangement has a fixed spatial relationship with the IOL such that when the at least one actuator or the at least one teeth arrangement moves the IOL moves with it, the at least one actuator being reversibly shiftable between a first three-dimensional shape when activated by the remote source energy, and a second three-dimensional shape when at rest, wherein said at least one actuator comprises a modifiable element formed by a shape memory material configured and operable to provide at least said first three-dimensional shape of the at least one actuator when said repositioning assembly is remotely activated by said remote energy source, the at least one actuator comprises a latch operable to selectively engage and disengage with the at least one teeth arrangement, when in said first and said second three-dimensional shapes respectively, such that when engaging the latch pushes against one tooth of the at least one teeth arrangement and causes a relative axial or angular incremental movement between the at least one actuator and the at least one teeth arrangement, thereby resulting in said controllable displacement of the IOL between two adjacent positions of said plurality of positions.

2. The lens support structure according to claim 1, wherein said repositioning assembly is configured to provide incremental transitions of said IOL between at least part of said plurality of positions.

3. The lens support structure according to claim 1, wherein said at least one actuator and said at least one teeth arrangement define(s) a ratchet mechanism such that said relative incremental movement occurs in only one direction in each of said at least one of the axial or angular directions, being respectively along or around the optical axis of the IOL.

4. The lens support structure according to claim 3, wherein said repositioning assembly comprises at least two actuators of said at least one actuator, each actuator of said at least two actuators being configured and operable to controllably displace the IOL in one of opposite directions either around or along the optical axis of the IOL.

5. The lens support structure according to claim 4, wherein said repositioning assembly respectively comprises at least two teeth arrangements of said at least one teeth arrangement, each of said at least two teeth arrangements interacts with one of said at least two actuators to thereby enable displacement of the IOL in opposite angular directions around the optical axis of the IOL.

6. The lens support structure according to claim 4, wherein said repositioning assembly comprises a single teeth arrangement that interacts with said at least two actuators to thereby enable displacement of the IOL in opposite axial directions along the optical axis of the IOL.

7. The lens support structure according to claim 1, wherein said at least one actuator comprises a spring element coupled to said modifiable element and being configured and operable to provide at least said second three-dimensional shape of the actuator when said repositioning assembly is not activated by said remote energy source.

8. The lens support structure according to claim 1, wherein said modifiable element comprises nitinol.

9. The lens support structure according to claim 1, wherein said remote energy source is configured and operable to provide heat to said at least one actuator of said repositioning assembly, thereby causing said reversible shifting of the at least one actuator between the first and the second three-dimensional shapes.

10. The lens support structure according to claim 9, wherein said remote energy source comprises a radiating element.

11. The lens support structure according to claim 9, wherein said remote energy source comprises a laser source.

12. The lens support structure according to claim 9, wherein said remote energy source comprises an electromagnetic radiation transmitter and said repositioning assembly comprises an electromagnetic radiation receiver.

13. The lens support structure according to claim 1, further comprising a fibrosis protector configured and operable to seal the repositioning assembly and prevent tissue invasion to the repositioning assembly while enabling user inspection and activation of the repositioning assembly.

14. A lens control system comprising the lens support structure of claim 1 and the remote energy source configured and operable to remotely activate said repositioning assembly, the lens control system being configured for controlling position of the intraocular lens.

15. The lens control system according to claim 14, wherein the remote energy source comprises at least one of the following: a heat generator, a laser beam generator, or an electromagnetic radiation transceiver.

16. An intraocular lens system comprising the lens support structure of claim 1 and the IOL integrally mounted in the lens support structure.

* * * * *